(12) United States Patent
Mander et al.

(10) Patent No.: US 10,092,272 B2
(45) Date of Patent: *Oct. 9, 2018

(54) HAND-HELD MEDICAL IMAGING SYSTEM WITH THUMB CONTROLLER AND ASSOCIATED APPARATUSES AND METHODS

(71) Applicant: FUJIFILM SonoSite, Inc., Bothell, WA (US)

(72) Inventors: Amanda Mander, Bainbridge Island, WA (US); Craig Chamberlain, Seattle, WA (US); Evan McCormack, Kenmore, WA (US); Sebastian Tomaszewski, Kenmore, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,219

(22) Filed: Oct. 3, 2017

(65) Prior Publication Data

US 2018/0021018 A1 Jan. 25, 2018

Related U.S. Application Data

(63) Continuation of application No. 14/256,759, filed on Apr. 18, 2014, now Pat. No. 9,801,613.

(51) Int. Cl.
*A61B 8/00* (2006.01)
*G06F 3/0482* (2013.01)
*G06F 3/0488* (2013.01)

(52) U.S. Cl.
CPC ............ *A61B 8/463* (2013.01); *A61B 8/4427* (2013.01); *A61B 8/465* (2013.01); *A61B 8/467* (2013.01);

(Continued)

(58) Field of Classification Search
CPC ....... A61B 8/463; A61B 8/4427; A61B 8/465; A61B 8/467; A61B 8/56; G06F 3/0482; G06F 3/04886

See application file for complete search history.

(56) References Cited

U.S. PATENT DOCUMENTS 9,538,985 B2 1/2017 Mander et al.
9,801,613 B2 * 10/2017 Mander .................. A61B 8/463
(Continued)

OTHER PUBLICATIONS

United States Patent and Trademark Office, Final Office Action, U.S. Appl. No. 14/256,759, dated Feb. 22, 2017, 8 pages.

(Continued)

*Primary Examiner* — Joel Lamprecht
(74) *Attorney, Agent, or Firm* — Perkins Coie LLP (57) ABSTRACT

A portable ultrasound system having a thumb controller is disclosed herein. A portable ultrasound system configured in accordance with one embodiment of the disclosure includes a transducer device and a hand-held base unit removably coupled to the transducer device. The base unit is configured to perform an ultrasound scan and to produce a split screen display. The split screen display includes an active image area at which images of a patient obtained from ultrasound signals received by the transducer device are displayed. The split screen display also includes a thumb control area that is accessible by a user's thumb when holding the portable ultrasound system. For example, the thumb control area can include a thumbwheel having one or more controls that can be selectively activated by the user's thumb when holding the portable ultrasound system and are rotatable on and off of the thumb control area.

14 Claims, 10 Drawing Sheets (52) U.S. Cl.
CPC ........ *G06F 3/0482* (2013.01); *G06F 3/04886* (2013.01); *A61B 8/56* (2013.01)

(56) References Cited

U.S. PATENT DOCUMENTS

| | | |
|---|---|---|
| 2002/0173721 A1 | 11/2002 | Grunwald et al. |
| 2005/0154303 A1 | 7/2005 | Walker et al. |
| 2008/0119731 A1 | 5/2008 | Becerra et al. |
| 2009/0043195 A1 | 2/2009 | Poland |
| 2010/0004539 A1 | 1/2010 | Chen et al. |
| 2010/0217128 A1 | 8/2010 | Betts et al. |
| 2012/0162078 A1 | 6/2012 | Ferren et al. |
| 2012/0232398 A1 | 9/2012 | Roham et al. |
| 2014/0098049 A1 | 4/2014 | Koch et al. |
| 2015/0297179 A1 | 10/2015 | Mander et al. |
| 2015/0297185 A1 | 10/2015 | Mander et al. |
| 2017/0095229 A1 | 4/2017 | Mander et al. |

OTHER PUBLICATIONS

United States Patent and Trademark Office, Final Office Action, U.S. Appl. No. 15/385,842, dated Dec. 8, 2017, 11 pages.
United States Patent and Trademark Office, Non-Final Office Action, U.S. Appl. No. 14/256,744, dated Mar. 11, 2016, 14 pages.
United States Patent and Trademark Office, Non-Final Office Action, U.S. Appl. No. 14/256,759, dated Jun. 29, 2016, 7 pages.
United States Patent and Trademark Office, Non-Final Office Action, U.S. Appl. No. 15/385,842, dated Jun. 28, 2017, 7 pages.
United States Patent and Trademark Office, Notice of Allowance, U.S. Appl. No. 14/256,744, dated Aug. 31, 2016, 5 pages.
United States Patent and Trademark Office, Notice of Allowance, U.S. Appl. No. 14/256,759, dated Jul. 3, 2017, 8 pages.

* cited by examiner

HAND-HELD MEDICAL IMAGING SYSTEM WITH THUMB CONTROLLER AND ASSOCIATED APPARATUSES AND METHODS

CROSS-REFERENCES TO RELATED APPLICATIONS

This application is a continuation U.S. patent application Ser. No. 14/256,759, filed on Apr. 18, 2014, and entitled "HAND-HELD MEDICAL IMAGING SYSTEM WITH THUMB CONTROLLER AND ASSOCIATED APPARATUSES AND METHODS," the disclosure of which is hereby incorporated herein in its entirety by reference.

TECHNICAL FIELD

The disclosed technology is related to medical imaging systems, and, in particular, some embodiments are related to portable ultrasound devices having a compact form factor and a user interface that facilitates hand-held operation.

BACKGROUND

Portable ultrasound imaging devices are used by anesthesiologists, emergency and critical care personnel, and other medical professionals. A portable ultrasound device can include a clamshell-type base unit having a handle for carrying the base unit. The base unit can fold open to a display and a keypad, and a user can connect an ultrasound transducer wand to the base unit to acquire and view ultrasound images on the display.

DETAILED DESCRIPTION

The following disclosure describes various types of hand-hand held imaging systems and associated apparatuses and methods. Certain details are set forth in the following description and FIGS. 1A-5 to provide a thorough understanding of various embodiments of the disclosure. Other details describing well-known structures and systems often associated with ultrasound systems, however, are not set forth below to avoid unnecessarily obscuring the description of the various embodiments of the disclosure.

Many of the details and features shown in the Figures are merely illustrative of particular embodiments of the disclosure. Accordingly, other embodiments can have other details and features without departing from the scope of the present disclosure. In addition, those of ordinary skill in the art will understand that further embodiments can be practiced without several of the details described below. Furthermore, various embodiments of the disclosure can include structures other than those illustrated in the Figures and are expressly not limited to the structures shown in the Figures. Moreover, the various elements and features illustrated in the Figures may not be drawn to scale.

In the Figures, identical reference numbers identify identical or at least generally similar elements. To facilitate the discussion of any particular element, the most significant digit or digits of any reference number refer to the Figure in which that element is first introduced. For example, element 120 is first introduced and discussed with reference to FIG. 1A.

Figure 1A:
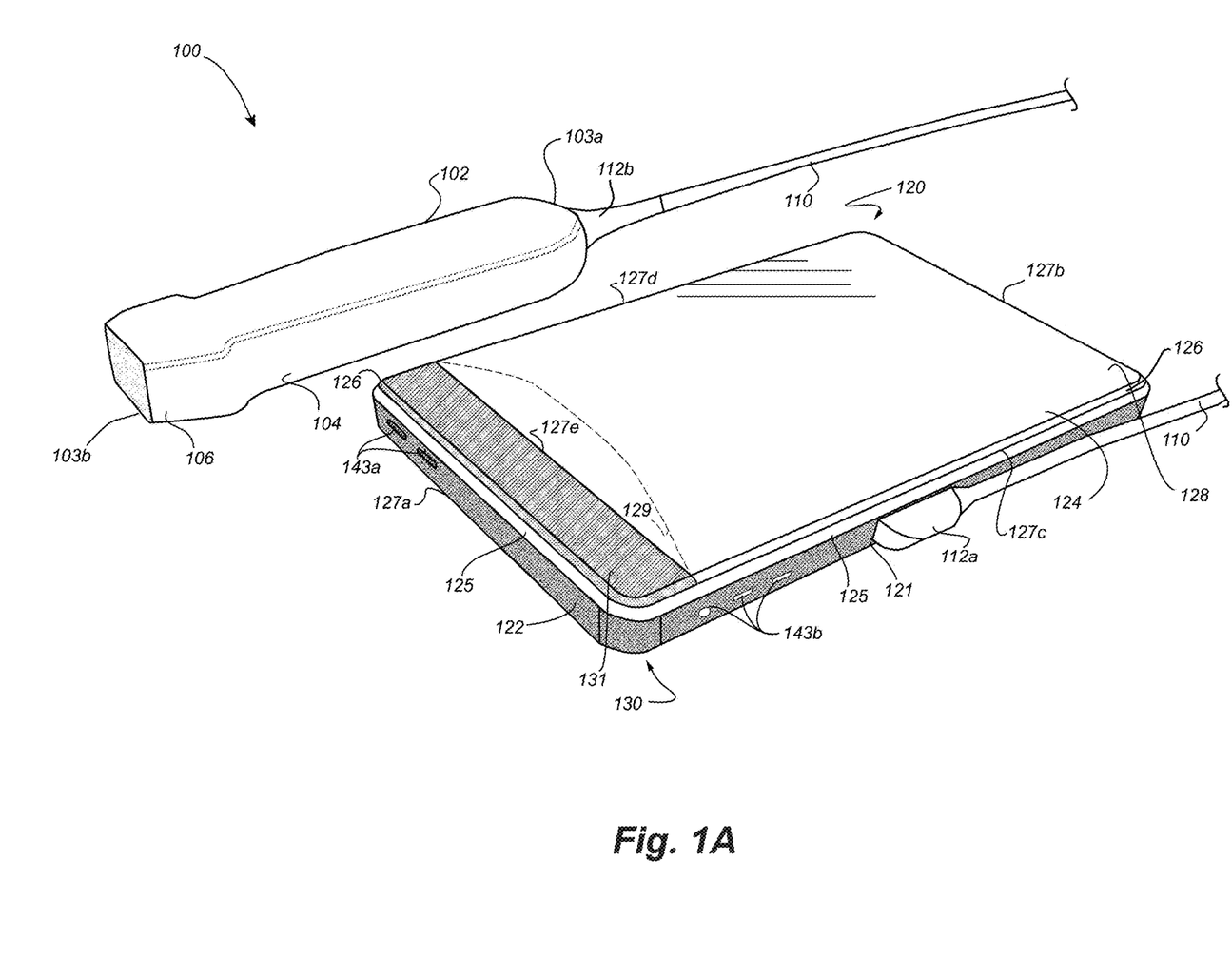
FIG. 1A is an isometric top view of a portable ultrasound system configured in accordance with an embodiment of the present disclosure.

FIG. 1A is an isometric top view of a portable ultrasound imaging system 100 ("portable system 100") configured in accordance with an embodiment of the present disclosure. The portable system 100 includes an ultrasound transducer device or a transducer wand 102 operably coupled to a hand-held base unit 120 ("base unit 120") by a signal cable 110. The signal cable 110 has a first end 112a and a second end 112b connected between a wand port 121 of the base unit 120 and a proximal end portion 103a of the transducer wand 102. In some embodiments, the signal cable 110 can include a connector or plug at the second end 112b (not shown) configured to removably couple the signal cable 110 to the transducer wand 102.

The transducer wand 102 includes a housing 104 (e.g., a molded plastic housing) extending from the proximal end portion 103a to a distal end portion 103b. The housing 104 includes a scan head region 106 that encloses a transducer array (not shown) within the housing 104 toward the distal end portion 103b. In some embodiments, the transducer wand 102 can include one or more buttons, triggers, or other input devices (not shown) configured, for example, to toggle power on or off, put the portable system 100 in a standby state, or to perform other operations. In other embodiments, the transducer wand 102 can include, for example, light-emitting elements that visually indicate an operational state of the transducer wand 102, a housing having a different shape and/or size, and/or other configurations or features.

In the illustrated embodiment, the base unit 120 includes a casing 122 (e.g., a plastic and/or metallic casing) and a touchscreen display 124 ("touchscreen 124") attached to the casing 122 by an outer band 125 (e.g., a plastic, rubber, and/or metallic band). In one embodiment, the outer band 125 can have a width in the range of about 0.25 cm to 1.5 cm (e.g., 1.0 cm). In another embodiment, the outer band 125 can include chamfered or filleted edges at opposite sides of the outer band 125 that conforms to the edges of the casing 122 and/or a front cover 126 of the touchscreen 124 to hold the front cover 126 to the casing 122. In some embodiments, the wand port 121, input controls 143a, and communication ports 143b can be located at the outer band 125. The input controls 143a can include, for example, buttons, knobs, switches, etc. The communication ports 143b can include, for example, audio, universal serial bus (USB), high-definition multimedia interface (HDMI) ports), etc.

The front cover 126 extends laterally across the front side of the base unit 120 from a first edge 127a (e.g., a left edge) of the base unit 120 to a second edge 127b (e.g., a right edge) opposite the first edge 127a. Although in the illustrated embodiment the front cover 126 extends across the entirety of the front side of the base unit 120, in other embodiments the front cover 126 can cover a smaller portion of the front side. The front cover 126 can include a glass or transparent plastic material covering a backlit panel (not shown) within the casing 122, such as a light emitting diode (LED) panel or a liquid crystal display (LCD) panel. A touchscreen surface 128 covers all or a portion of the front cover 126. In one embodiment, the touchscreen surface 128 includes transparent electrodes (e.g., indium tin oxide electrodes; not shown) in a capacitive configuration for sensing skin or stylus contact with the touchscreen surface 128. In another embodiment, the touchscreen surface 128 can include electrodes in a resistive configuration configured to sense pressure contact (rather than skin contact). In one aspect of this embodiment, a resistive configuration can enable a user to operate the touchscreen 124 with a gloved hand (e.g., a latex-gloved hand).

The base unit 120 unit also includes a handle region 130 toward the first edge 127a of the base unit 120 and adjacent to the touchscreen 124. In the illustrated embodiment of FIG. 1A, the handle region 130 includes a top handle surface 131 formed on a portion of the front cover 126 adjacent to the touchscreen surface 128. The top handle surface 131 can include, for example, a laminate, coating, or other suitable surface treatment (e.g., a textured surface treatment) that extends between third and fourth edges 127c and 127d of the base unit 120 that are each generally transverse to the first and second edges 127a and 127b. The top handle surface 131 spans across a portion of the front cover 126 between the first edge 127a and a first interior edge 127e of the top handle surface 131 toward the touchscreen surface 128. In the illustrated embodiment, the first interior edge 127e is generally linear and extends between the third and fourth edges 127c and 127d. In other embodiments, however, the first interior edge 127e can have a curved shape, as shown, for example, by dashed line 129. In one embodiment, such a curved shape can expand the top handle surface 131 to accommodate the wider portion of a user's palm, while still maximizing the size of the touchscreen 124 at the front cover 126.

In one aspect of this embodiment, the top handle surface 131 facilitates a user's grip with the handle region 130 when holding the base unit 120. For example, the top handle surface 131 can enhance tactility to facilitate a user's grip. In another aspect of this embodiment, the top handle surface 131 is configured to insulate and/or space a user's palm apart from the touchscreen surface 128. Accordingly, users can hold the base unit 120 at the handle region 130 with their fingers underneath the base unit 120 and their thumb on the top handle surface 131. When holding the base unit 120 in such a manner, the user's palm can be prevented from making contact with or otherwise interfering with the touchscreen surface 128 during operation.

Figure 1B:
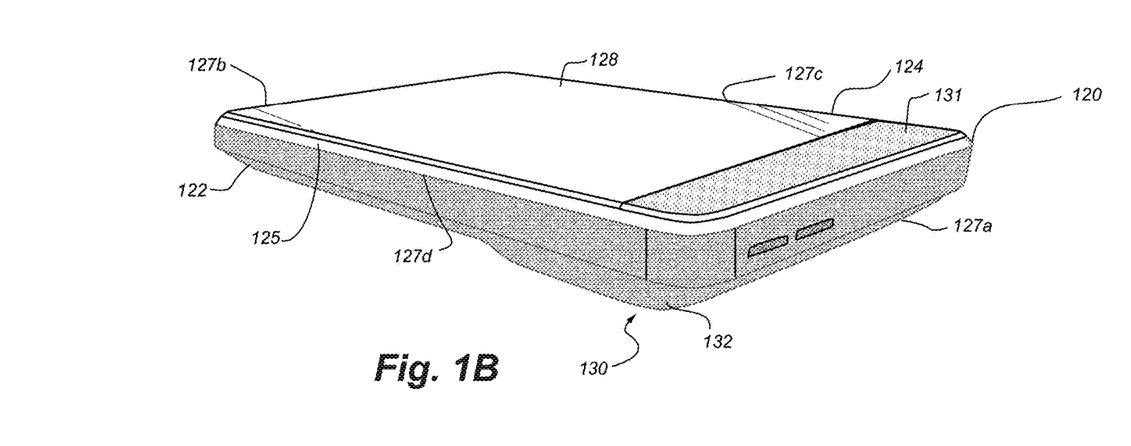
FIG. 1B is an isometric side view and FIG. 1C is an isometric bottom view of a base unit of the portable ultrasound system of FIG. 1A showing a handle region of the base unit in more detail.
Figure 1C:
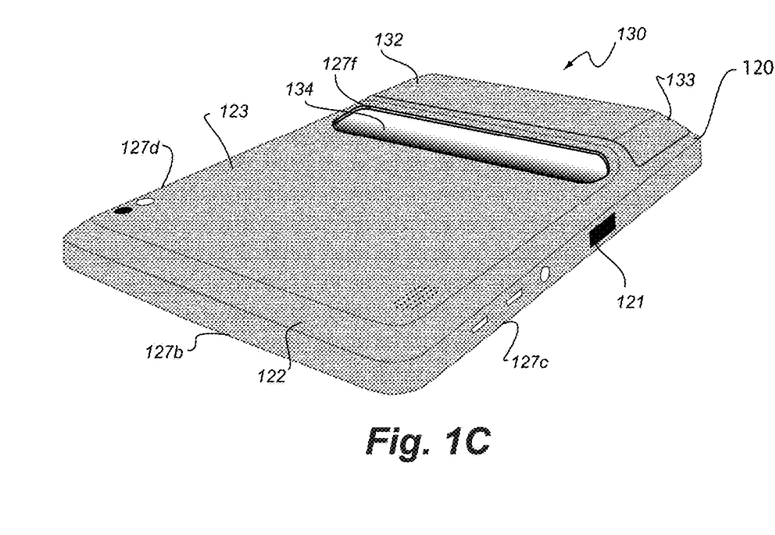

FIG. 1B is an isometric side view and FIG. 1C is an isometric bottom view of the base unit 120 showing the handle region 130 in more detail. Referring to FIGS. 1B and 1C together, the handle region 130 includes a raised grip member 132 at a backside of the casing 122 and toward the first edge 127a. The grip member 132 extends between the third and fourth edges 127c and 127d of the base unit 120 and projects outwardly away from a backside surface 123 of the casing 122 (in, e.g., the shape of a mesa). The grip member 132 includes an internal cavity that defines a battery compartment (not visible in FIGS. 1B and 1C) and which is covered by a removable battery cover 133. The grip member 132 also includes a concave, elongated depression 134 that extends along a second interior edge 127f of the grip member 132. The depression 134 projects into the backside surface 123 and also into a portion of the grip member 132 toward the second interior edge 127f to receive a user's fingers for holding the base unit 120. In some embodiments, the grip member 132 can be covered with an elastomeric material or other surface treatment that also enhances the user's grip.

Figure 1D:
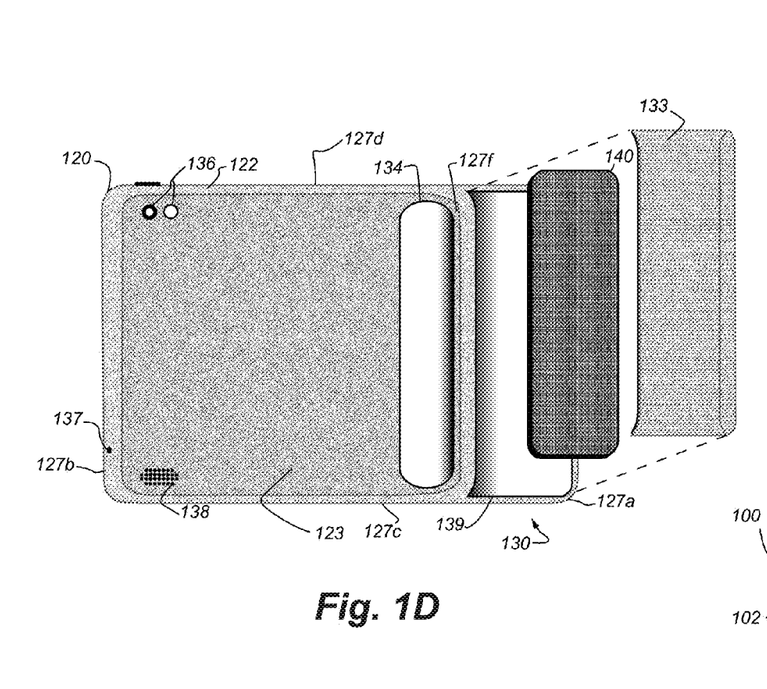
FIG. 1D is a partially-exploded bottom view of the base unit of the portable ultrasound system of FIG. 1A showing certain features of the base unit in more detail.

FIG. 1D is a partially-exploded bottom view of the base unit 120 showing certain features of the base unit in more detail. For example, the base unit 120 can include apertures or perforations for a camera 136 (e.g., a lens and a flash), a microphone 137, and a speaker 138. As described in greater detail below, a user can employ the camera 136, the microphone 137, and/or the speaker 138 to interact with a remote party, such as a colleague, while operating the base unit 120.

As further shown in FIG. 1D, the battery cover 133 covers a battery compartment 139 containing a battery 140 (e.g., a rechargeable battery). In some embodiments, the battery compartment 139 can house other components (not shown) in addition to the battery 140, such as removable memory (e.g., a memory stick), data ports, a stylus, etc. In addition to powering the base unit 120, the battery 140 can be configured to provide weight (or mass) to the handle region 130 to bias the center of mass of the base unit 120 toward the handle region 130. In one aspect of this embodiment, the biased center of mass can enable the operator to securely and comfortably hold the base unit 120 with a single hand at the handle region 130. For example, the biased center of mass can counteract against torque or torsional forces that might otherwise cause hand and/or wrist strain.

Figure 1E:
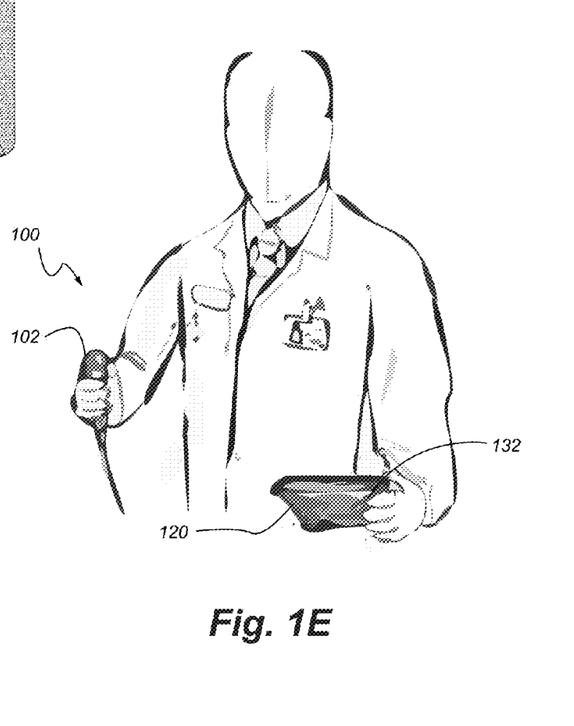
FIG. 1E shows a user carrying the portable ultrasound system of FIG. 1A in accordance with an embodiment of the present disclosure.

FIG. 1E shows a user carrying the portable system 100 in accordance with an embodiment of the present disclosure. In use, a physician or ultrasound technician can use the transducer wand 102 and the base unit 120 to perform an ultrasound scan. In particular, the user can place the transducer wand 102 toward a target region of interest within a patient (e.g., an organ and/or an internal cavity), and the base unit 120 can display an image on the touchscreen 124 (FIG. 1A) based on the ultrasound scan. In one aspect of this embodiment, a user can use one hand (e.g., the right hand) to operate the transducer wand 102 and simultaneously use the other hand (e.g., the left hand) to carry and operate the base unit 120. To carry and operate the base unit 120 in such a manner, the user's fingertips ergonomically fit within the depression 134 with the thumb extending over the front cover 126 (FIG. 1A) of the base unit 120. In this position, a portion of the user's palm (e.g., the thenar portion of the palm) can press against the top handle surface 131 (FIG. 1A) and the tip of the user's thumb if free to move across and into contact with a portion of the touchscreen 124 (FIG. 1A). As described in greater detail below, in some embodiments the touchscreen 124 can include a graphical thumb controller (not visible in FIG. 1E) configured to control the base unit 120.

Figure 2:
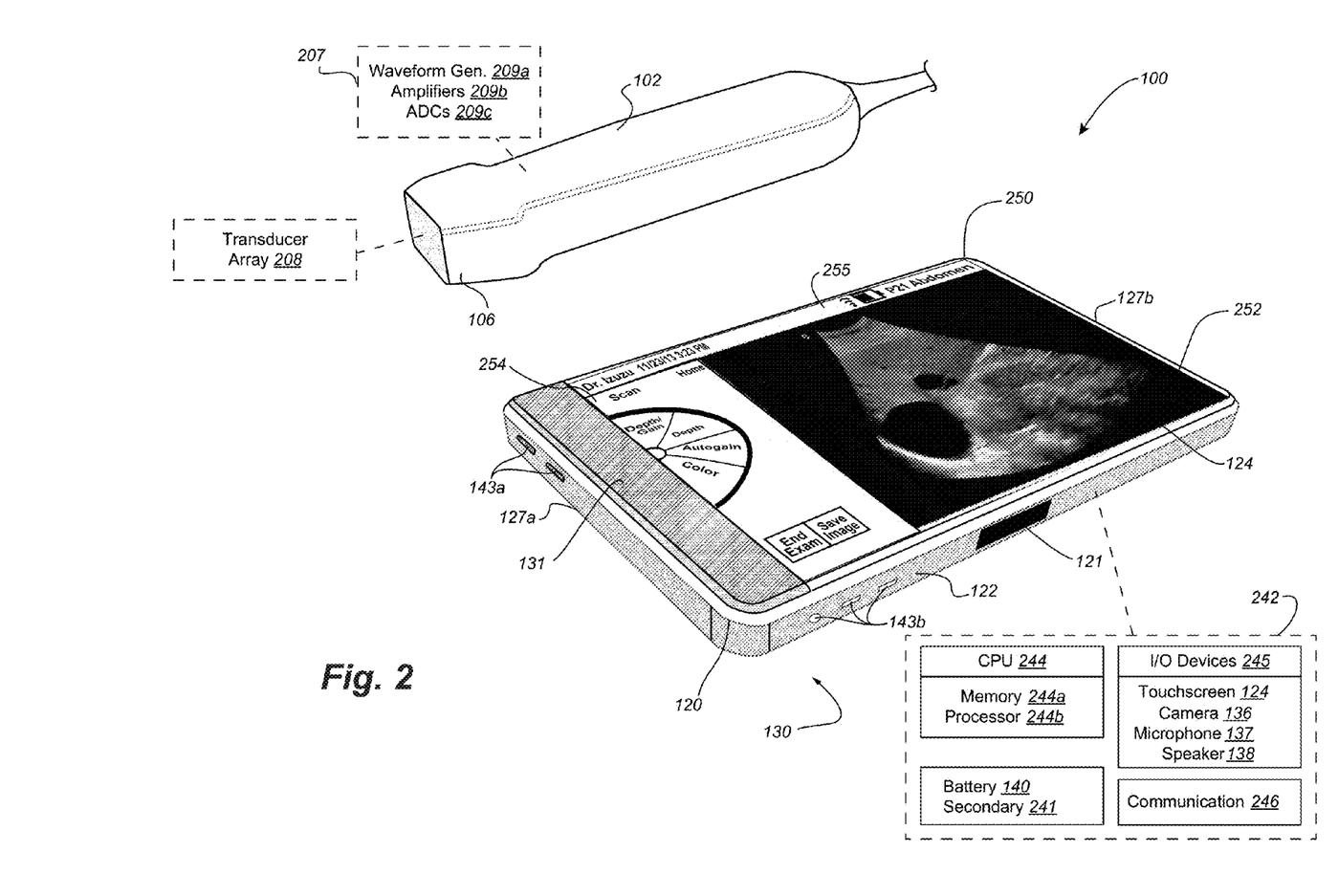
FIG. 2 is a partially schematic, isometric view of the portable ultrasound system of FIG. 1A showing transducer electronics and display electronics of the portable system.

FIG. 2 is a partially schematic, isometric view of the portable system 100 showing transducer electronics 207 of the transducer wand 102 and base unit electronics 242 of the base unit 120. As shown schematically, the transducer electronics 207 are operably coupled to a transducer array 208 positioned at the scan head region 106. The transducer array 208 can include, for example, an array of microelectromechanical transducer elements configured to transmit an acoustic signal and receive a return signal to and from a target region of interest. The transducer electronics 207 can include, for example, waveform generators 209a, amplifiers 209b, analog to digital converts (ADCs) 209c, and other ultrasound signal processing components (e.g., a CPU, controller, transmit/receive beam former circuitry, etc.). In one embodiment, the transducer electronics 207 can communicate digitally with the base unit 120 (i.e., over the signal cable 110 shown in FIG. 1A). In another embodiment, the transducer electronics 207 can exchange analog signals with the base unit 120.

The base unit electronics 242 are operably coupled to the wand port 121, the input controls 143a, and the communication ports 143b of the base unit 120. The base unit electronics 242 include a CPU 244, input/output devices 245, and communication components 246. The input/output devices 245 include the touchscreen 124 and can also include, for example, the camera 136, the microphone 137, and/or the speaker 138. The communication components 246 can include, for example, signal buses, network adaptors, wireless transceivers (e.g., Wi-Fi, cellular or other radio transceivers), etc. The CPU 244 includes a memory 244a and a programmable processor 244b configured to execute instructions in the memory 244a in order to perform various processes, logic flows, and routines.

The base unit electronics 242 are powered by the battery 140. In one embodiment, the battery 140 can also power the transducer wand 102 via the signal cable 110 of FIG. 1A. In another embodiment, the transducer wand 102 can include a separate battery or power source (not shown) configured to independently power the transducer electronics 207 and the transducer array 208. For example, a wireless transducer wand can include a separate power supply for powering the wireless wand. In one aspect of the illustrated embodiment, the base unit 120 can be powered by a secondary power component 241, such as a second battery, a capacitor, a photovoltaic panel, etc. The secondary power component 241 can be configured, for example, to provide reserve power and/or maintain the base unit 120 in a standby state. For example, the secondary power component 241 can temporarily power the base unit 120 when the charge level of the battery 140 becomes low.

In the illustrated embodiment, the touchscreen 124 presents a split screen, graphical user interface 250 containing an active image area 252 and a thumb control area 254. The user can activate one or more controls positioned in the thumb control area 254 to control an ultrasound scan. The user can use the active image area 252 to view the resultant ultrasound image. The graphical user interface 250 can also include a status bar 255 that contains, for example, text and/or graphics corresponding to a status, such as the time and date, the device user, wireless signal strength, remaining battery life, and/or other information. For example, the status bar 255 in FIG. 2 includes text that identifies the "abdomen" as the target region of interest.

In operation, the transducer wand 102 can perform an ultrasound scan of the target region of interest and the base unit 120 can produce an ultrasound image (or a series of images) of the target region on the touchscreen 124. In particular, the base unit electronics 242 can communicate control signals to the transducer electronics 207. The transducer electronics 207 can in turn use the control signals to operate the transducer array 208, and the transducer array 208 can produce return signals (or ultrasound signals) containing ultrasound information that the base unit 120 uses to ultimately produce the ultrasound image at the touchscreen 124. In the illustrated embodiment, the touchscreen 124 presents a graphical user interface 250 containing an active image area 252 and a thumb control area 254. The user can activate one or more controls positioned in the thumb control area 254 to control the ultrasound scan. The user can use the active image area 252 to view the resultant ultrasound image.

Figure 3A:
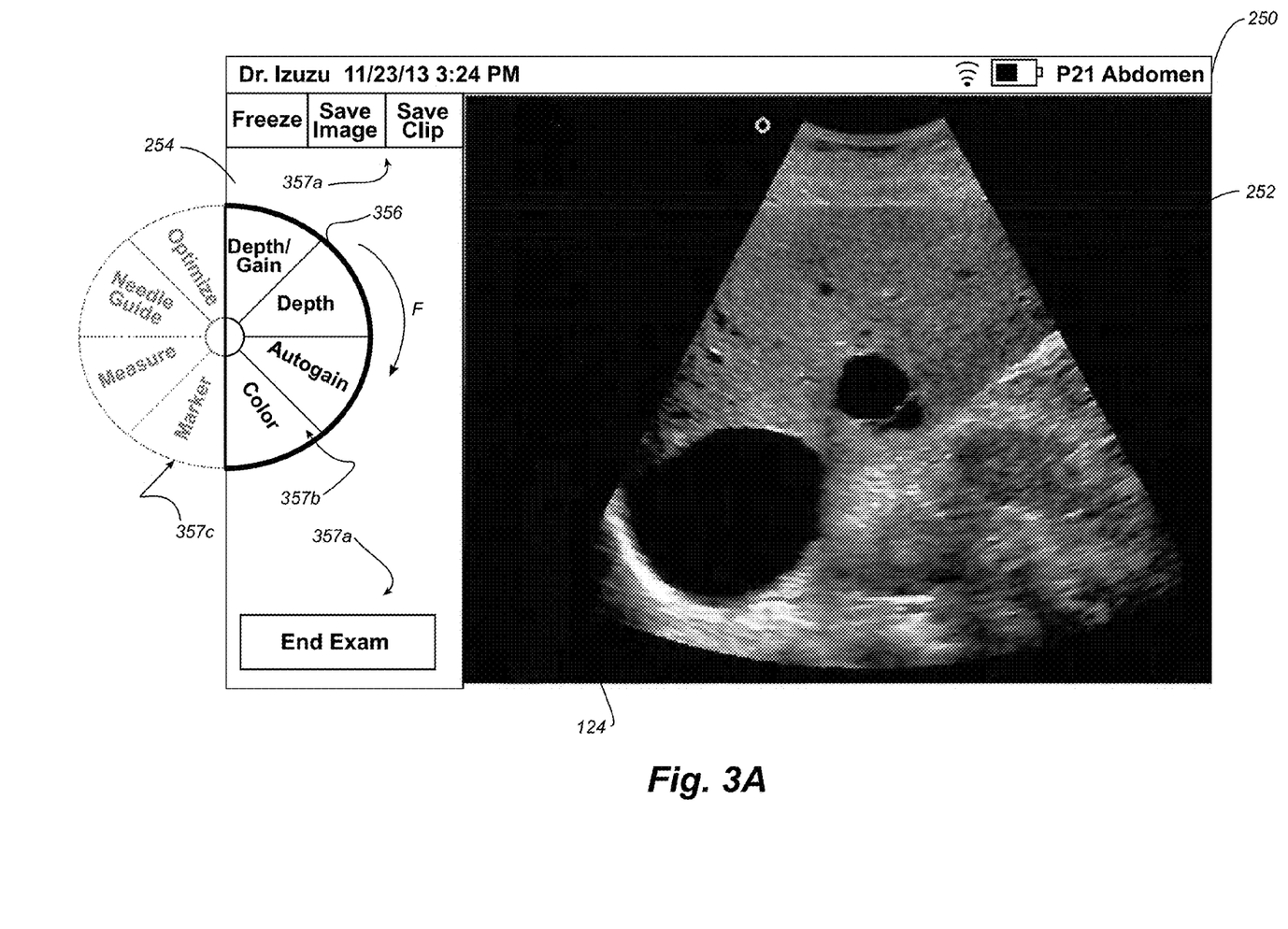
FIGS. 3A-3D show a graphical control area of the portable ultrasound system of FIG. 1A in various display states in accordance with several embodiments of the present disclosure.

FIGS. 3A-3D show the thumb control area 254 of the base unit 120 (FIG. 1A) in various display states in accordance with several embodiments of the present disclosure. Referring first to FIG. 3A, the thumb control area 254 includes a number of soft buttons or controls, such as a thumbwheel 356 and soft buttons 357 (identified individually as a first, second, and third group of soft buttons 357a-357c). In the illustrated embodiment, the first group of soft buttons 357a is located outside of the thumbwheel 356, the second group 357b is located on-screen and on the thumbwheel 356, and the third group 357c is also on the thumbwheel 356, but off-screen. Although shown in the illustrated embodiment as touch-selectable panels, in other embodiments the thumb control area 254 can employ other touch-selectable features in addition to or in lieu of the soft buttons 357, such as user-selectable graphical icons.

In operation, the touch-selectable features enable users to adjust various operating parameters of the ultrasound system. For example, to enable ultrasound scanning, a user can select soft buttons labeled "Scan." To control gain or scan depth, the user can select soft buttons labeled "Depth/Gain," "Depth," or "Autogain." To change the scan mode to color power Doppler (CPD) mode, the user can select a soft button labeled "Color." To enable a needle biopsy mode, the user can select a soft button labeled "Needle Guide." To overlay a marker or a measurement tool on an ultrasound image, the user can select soft button labeled "Marker" or "Measure." To adjust viewing angle, brightness, contrast, etc. the user can select a soft button labeled "Optimize."

The thumbwheel 356 allows the user to access other soft buttons not in view on the touchscreen 124. For example, users can use their thumb to sweep over the soft buttons displayed in order to rotate the thumbwheel 356 in the clockwise direction (as shown, e.g., by Arrow F) and bring at least a portion of the third group of soft button 357c into view. In one embodiment, the user can rotate the thumbwheel 356 by touching the thumbwheel 356 at its outer edge or periphery (i.e., via the touchscreen 124) and then spinning the thumbwheel 356 until a desired soft button comes into view. In some embodiments, the thumbwheel 356 can allow the user to control all aspects of ultrasound imaging. For example, the thumbwheel 356 can select soft buttons that open sub-menus or secondary thumbwheels containing different soft buttons corresponding to different functions. In one embodiment, the thumbwheel can present soft buttons in an order indicative of their frequency of use. For example, in the illustrated embodiment, the "Color" soft button is positioned between the "Autogain" soft button and the "Marker" soft button. However, if the user were to use the marker feature of the base unit 120 more frequently than color Doppler mode, the processor could exchange the positions of the "Color" soft button and the "Marker" soft button such that the latter is presented between the "Color" and "Autogain" soft buttons. If the user were to begin using Color Doppler mode more frequently, the locations of the buttons could again be exchanged. In one aspect of this embodiment, the locations of the soft buttons on the thumbwheel can be dynamically updated such that the user can access the most frequently used soft buttons with limited rotation of the thumbwheel 356. In an additional or alternate embodiment, the user can customize the location of the soft buttons on the thumbwheel and/or the size/shape of the soft buttons. Also, as described in greater detail below, the thumb control area 254 can present other control features to the user, such as a graphical slider feature to modify, augment, or otherwise control operation of the base unit 120.

Figure 3B:
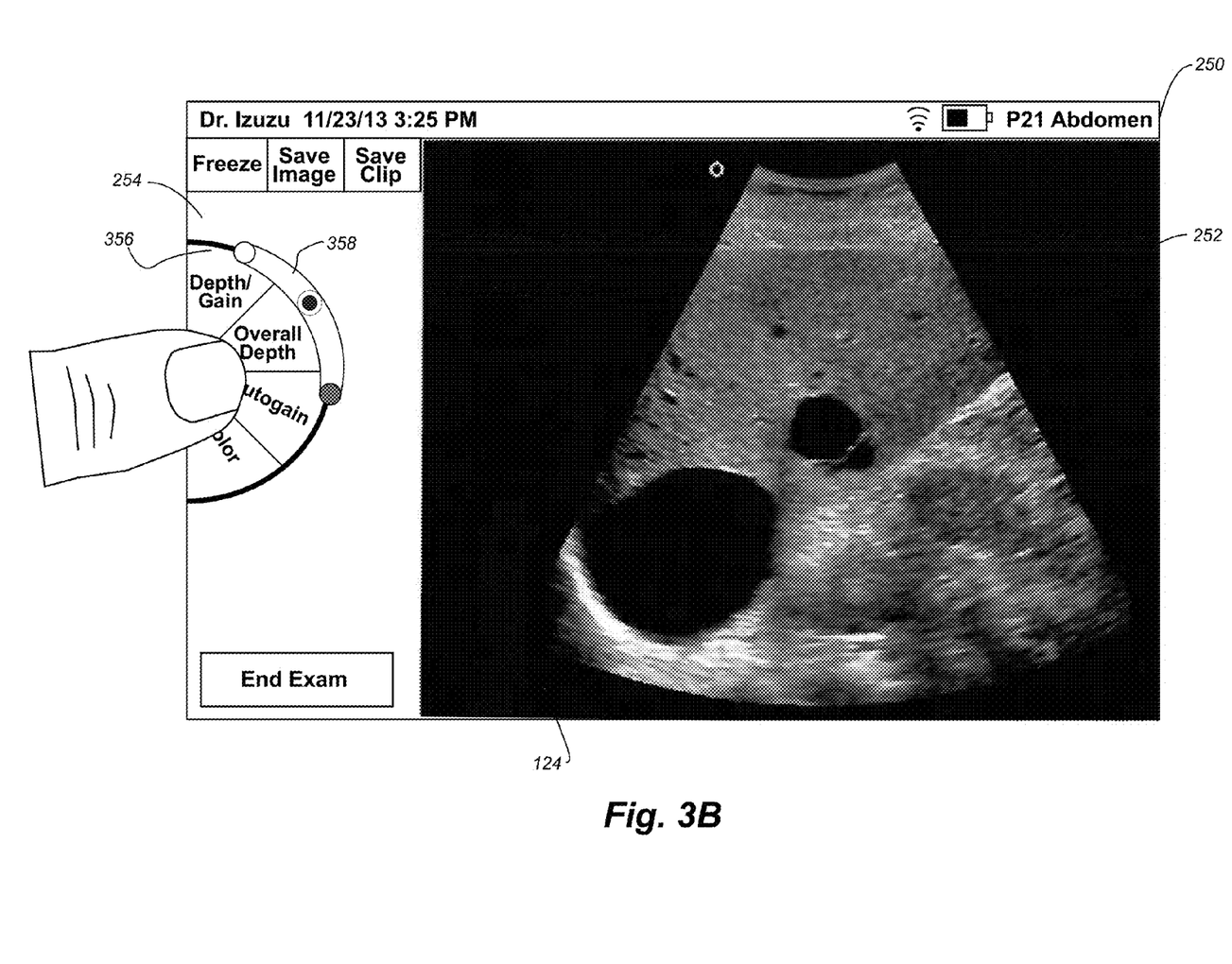

Referring to FIG. 3B, once the user makes a desired selection, a processor of the base unit 120 (e.g., the processor 244b; FIG. 2) can introduce one or more additional control features adjacent to the thumbwheel 356 or at other suitable locations that are accessible to the user's thumb. For example, in response to the user selecting "Depth," (FIG. 3A) a graphical slider feature 358 is presented at the periphery of the thumbwheel 356. In this embodiment, the user can use the slider feature 358 to modify the overall gain of the ultrasound scan. To decrease gain, for example, the user's thumb can touch the slider feature 358 and move in a curved, clockwise path across the slider. Alternatively, to increase gain the user's thumb can move in a curved, counter-clockwise path across the slider. In some embodiments, the shape of a control feature is indicative of its function. For example, in some embodiments the slider feature 358 can narrow toward one end to signify less gain and taper to have a wider area toward another end where gain is increased. In other embodiments, color or visual texture could be used to indicate how the feature affects the functions controlled.

Figure 3C:
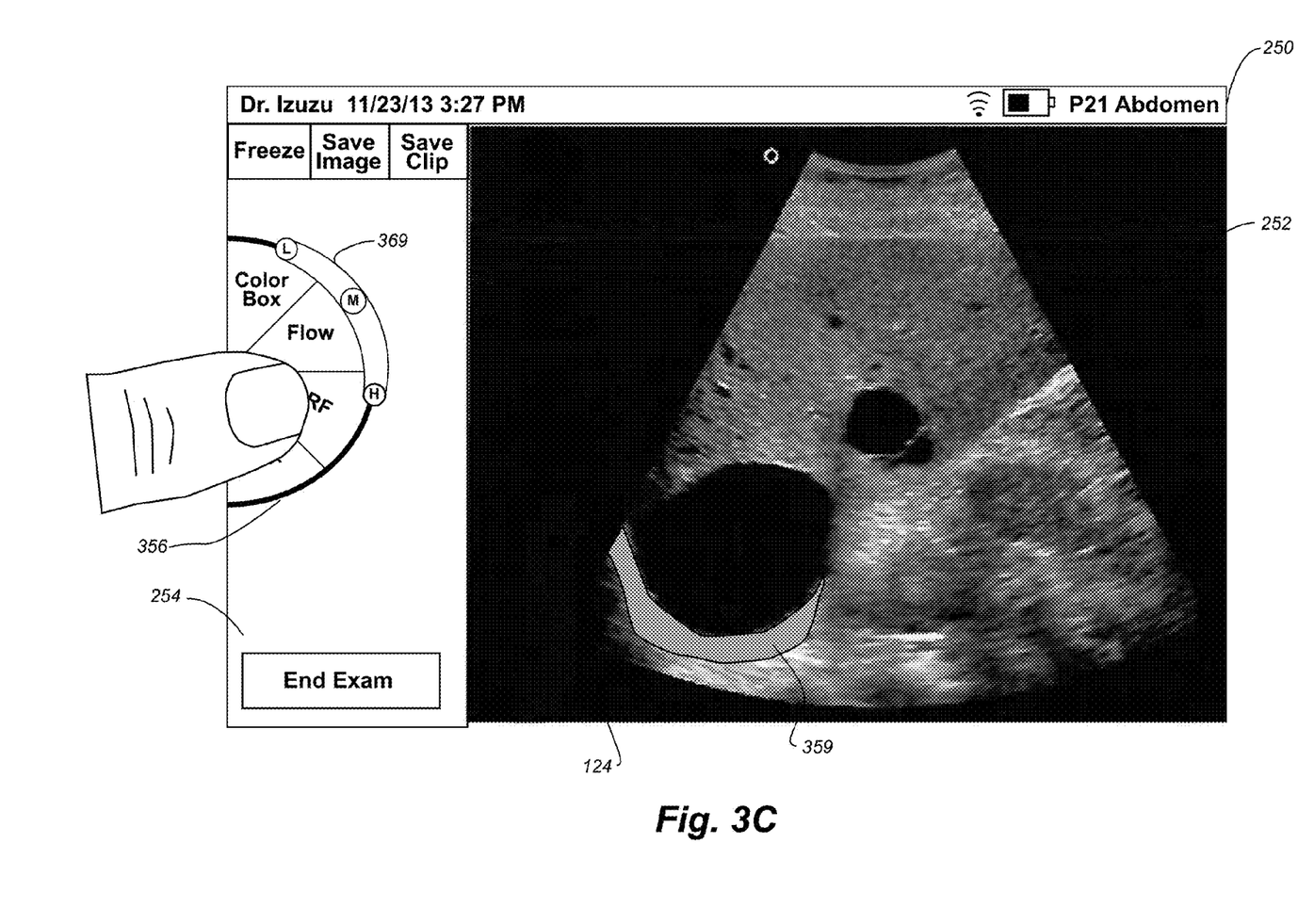

FIG. 3C shows the thumb control area 254 in a configuration in which a user has selected the "Color" soft button for applying a color to an ultrasound image. For example, colors can be overlaid on an ultrasound image to show, e.g., speed and direction of blood flow through a blood vessel or blood flow through vessels within solid organs. In the illustrated embodiment, the processor presents a slider feature 369 adjacent the thumbwheel 356 and an overlaying feature 359 on the image of the image area 252. In one aspect of this embodiment, the user can assign a particular color to the region of interest, such as a region of high (H), medium (M), and/or low (L) blood flow.

Figure 3D:
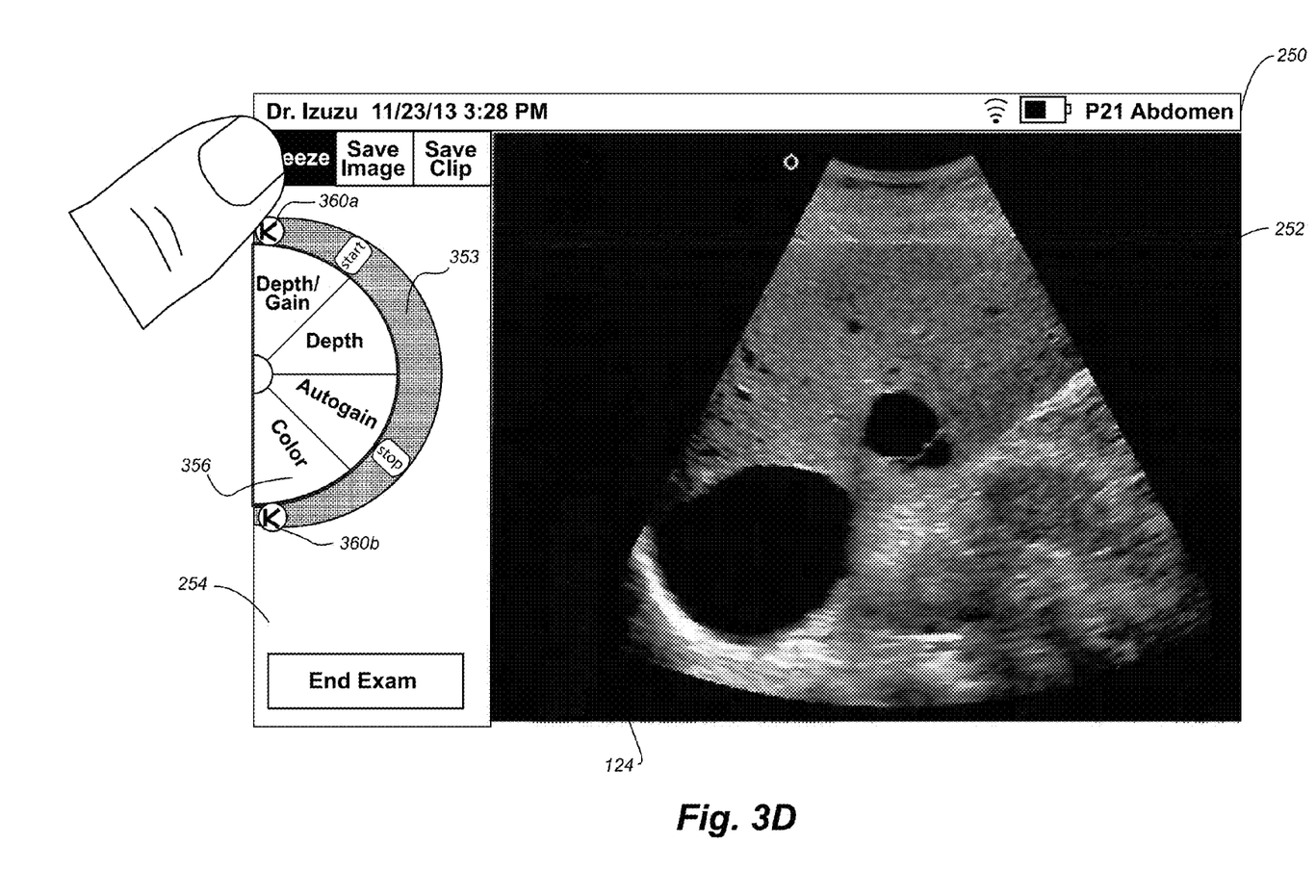

FIG. 3D shows the thumb control area 254 in a configuration for capturing and saving an ultrasound image frame or a series of frames (e.g., an image clip). In this display state, the user has selected a "Freeze" button to suspend live scanning. In response, the processor has presented a slider feature 353 adjacent to the thumbwheel 356. In this embodiment, the user can use the slider feature 353 to advance or rewind through a series of image frames. To rewind, for example, the user's thumb can move in a counter-clockwise path across the slider feature 353. Alternatively, to advance forward through the frames the user's thumb can move in a clockwise path across the slider feature 353. In the illustrated embodiment, the slider feature 353 also includes a rewind button 360a and a forward button 360b. The user can use the rewind and forward buttons 360a and 360b in lieu of the slider feature 353. In one embodiment, the user can select the rewind and forward buttons 360a and 360b to advance or rewind in increments of a single frame (with, e.g., a single tap of either of the buttons 360a and 360b). In another embodiment, the user can hold (i.e., rather than tap) either of the buttons 360a and 360b to rapidly move through frames.

In the illustrated embodiment of FIG. 3D, the thumb control area 254 also includes "Start" and "Stop" tabs that are within the slider feature 353. The user can select the "Start" tab to mark the beginning of an image clip, and the user can select the "Stop" tab to mark the end of the clip. Once marked, the user can select the "Save" button to save the imaging clip to the base unit.

Figure 4:
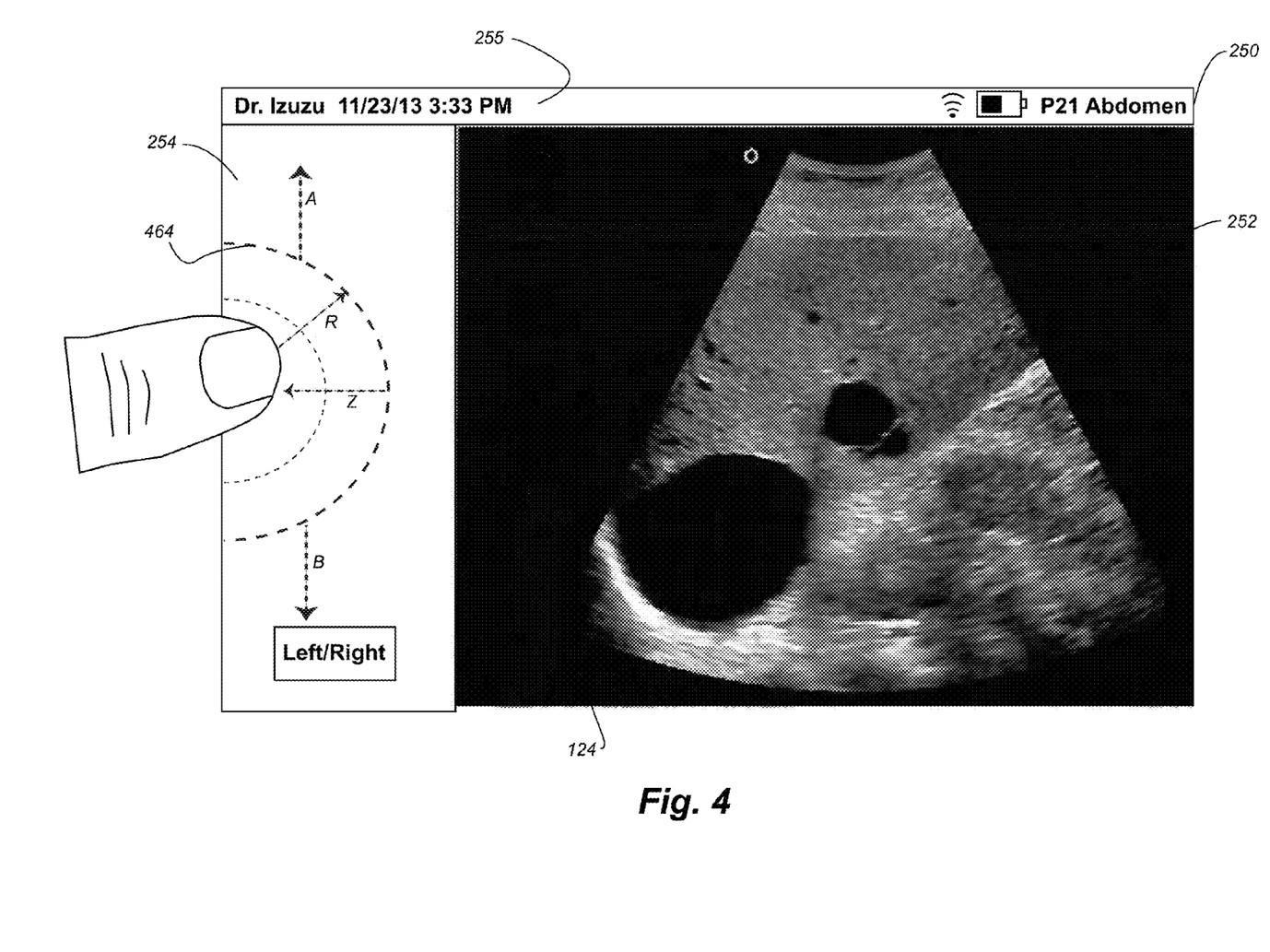
FIG. 4 shows a user configuration screen of the thumb control area of FIGS. 3A-3D configured in accordance with an embodiment of the present disclosure.

FIG. 4 shows a user configuration screen of the thumb control area 254 of the base unit 120 (FIG. 1A) configured in accordance with an embodiment of the present disclosure. In one embodiment, the user can touch and hold the thumbwheel 356 for one or more seconds to access the configuration screen. In the configuration screen, the processor presents a "Left/Right" soft button and a thumbwheel silhouette 464. The user can toggle the "Left/Right" button to enable left-handed or right-handed operation. In particular, when the user toggles the "Left/Right" button, the controls and labels on the touchscreen 124 can be inverted so that the user can rotate the base unit 120 and then operate it with a different hand.

The thumbwheel silhouette 464 enables the user to set the position and size (radius) of the thumbwheel 356. For example, in the illustrated embodiment the user can move the thumbwheel silhouette upwardly 464 (as shown, e.g., by arrow A) or downwardly (as shown, e.g., by arrow B) to set the position of the thumbwheel 356 in the thumb control area 254. The user can also slide the thumbwheel silhouette 464 radially outward to increase thumbwheel size (as shown e.g., by arrow R) or radially inward to reduce thumbwheel size (as shown, e.g., by arrow Z). Once the user has selected the position and size of the thumbwheel silhouette 464, the user can tap or double tap the thumbwheel silhouette 464 to confirm the thumbwheel position and size and exit the configuration screen.

In one aspect of this embodiment, a user with a smaller hand can employ a small thumbwheel positioned toward the center of the thumb control area 254, while a user with a larger hand can employ a relatively larger thumbwheel disposed more proximate to the status bar 255. In general, the user can configure the thumbwheel to that particular user's range of thumb motion to reduce or alleviate hand strain or fatigue. In another aspect of this embodiment, the user can set the position, size, and/or orientation of the other features of the thumb control area 254. For example, the position and size of a slider feature can be scaled according to the position and size that the user sets for the thumbwheel.

Figure 5A:
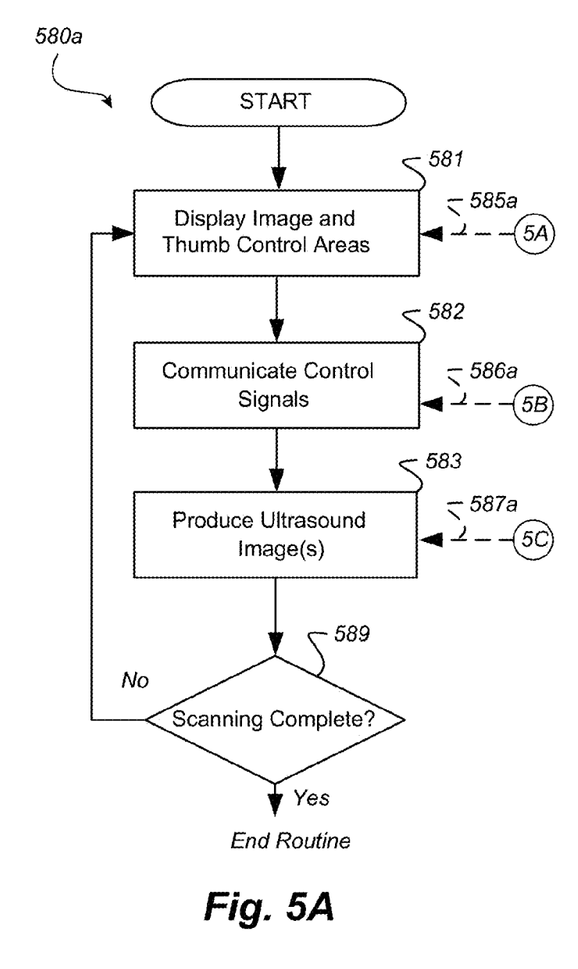
FIG. 5A is a flow diagram illustrating a routine for producing an image at an image area.
Figure 5B:
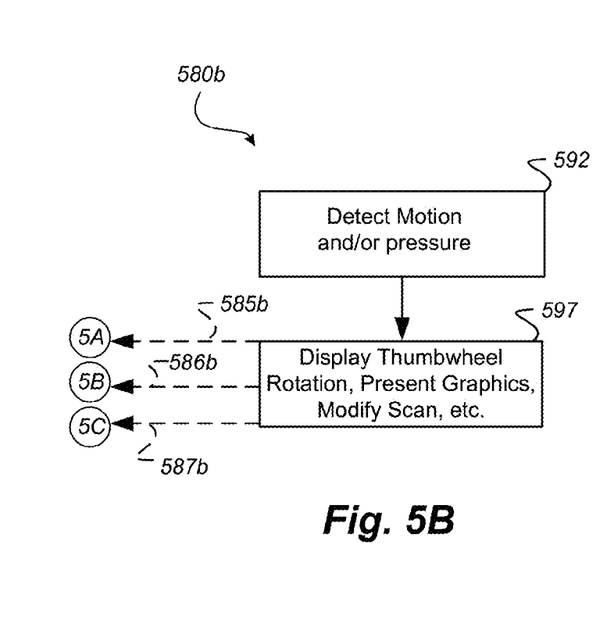
FIG. 5B is a flow diagram for modifying the image via a graphical user interface in accordance with several embodiments of the present disclosure.

FIG. 5A is a flow diagram illustrating a routine 580a for producing an image at the image area 252 (FIG. 2), and FIG. 5B is a flow diagram 580b for modifying the image via the graphical user interface 250 in accordance with several embodiments of the present disclosure. Referring to FIG. 5A, after the start block, the routine 580 proceeds to block 581 to display the graphical user interface 250 (FIG. 2) at the touchscreen 124. For example, the routine 580 can proceed to block 581 when the user initiates an active scan mode and/or an image/clip capture mode. In some embodiments, the graphical user interface 250 can display a blank screen or other screen image (e.g., a background screen or splash screen) until the base unit 120 enters one of these modes. Once the graphical user interface 250 is displayed, the routine 580 proceeds to block 582.

At block 582, the routine 580a can communicate control signals to the transducer wand 102. In particular, the control signals can instruct the transducer electronics 207 (FIG. 2) to begin ultrasound imaging. The transducer electronics 207 can in turn use the control signals to operate the transducer array 208 (FIG. 2), and the transducer array 208 can produce return signals (or ultrasound signals) containing ultrasound information. At block 583, the routine 580 receives the ultrasound signals and produces an ultrasound image (or a series of images) at the active image area 252 (FIG. 2). The routine 580a also receives input via the graphical user interface 250, as shown by dashed arrows 585a-587a, respectively. More specifically, the routine 580 receives input while concurrently displaying the image and thumb control areas (block 581), producing control signals (block 582), and/or producing ultrasound images (block 583).

Referring to FIG. 5B, at block 592 the routine 580b can detect for motion on the thumbwheel 356 and/or motion on a graphical feature (block 592), such as a thumbwheel, graphical slider feature, soft button, etc. If the routine 580b detects motion and/or pressure on the thumbwheel 356, for example, the routine 580b can rotate the thumbwheel 356 to bring controls (e.g., soft buttons) onto and off the thumb control area 254. If the routine 580b detects selection of a control that employs a slider feature 353, for example, the routine 580b can display the slider feature. The routine 580b can likewise display graphical movement within or on the slider feature depending on the detected motion. In addition, the routine 580b can determine if other touch-selectable features have been selected based on motion and/or pressure (e.g., selection of a soft button not on the thumbwheel). Once the routine 580 ultimately detects a user input, the routine 580b can then proceed to block 597 to provide an appropriate response.

At block 597, the routine 580b can adjust, modify, or otherwise control, for example, a scan parameter, a display property, and/or other operational aspect of the portable ultrasound system 100. If the detected movement and/or pressure relates rotation of the thumbwheel or the presentation of a graphical slider, for example, the routine 580b can modify the corresponding presentation on the thumb control area 252, as shown by dashed arrow 585b. For example, in response to clockwise motion of the user's thumb detected at the thumbwheel 356 (FIG. 3A), the routine 580b can show the rotation of the thumbwheel and soft buttons that come into and out of view. If the user input relates to a modification of the ultrasound scan, the routine 580b can modify the control signals communicated to the transducer wand 102, as shown by dashed arrow 586b. For example, in some embodiments the routine 580b can change at least one of gain, scan depth, and imaging mode of the ultrasound scan. In other embodiments, the routine 580b can modify a display property (e.g., color, contrast, brightness, etc.), overlay a graphic, or otherwise modify or update the graphical user interface 250, as shown by dashed arrow 587b.

Referring again to FIG. 5A, when ultrasound imaging is complete (block 589), the routine 580a can terminate. In some embodiments, the routine 580a can terminate when the user exits an ultrasound scanning mode at the base unit 120 and returns to a home screen.

From the foregoing, it will be appreciated that specific embodiments of the disclosure have been described herein for purposes of illustration, but that various modifications may be made without deviating from the scope of the various embodiments of the present disclosure. Moreover, because many of the basic structures and functions of transducer arrays, transducer electronics, and other processor electronics are known, they have not been shown or described in further detail to avoid unnecessarily obscuring the described embodiments. Further, while various advantages and features associated with certain embodiments of the disclosure have been described above in the context of those embodiments, other embodiments may also exhibit such advantages and/or features, and not all embodiments need necessarily exhibit such advantages and/or features to fall within the scope of the disclosure.

The invention claimed is:

1. A portable ultrasound system, comprising:
   a transducer device; and
   a hand-held base unit removably coupled to the transducer device and configured to perform an ultrasound scan, wherein the base unit includes—
      a touchscreen display,
      a programmable processor, and
      a non-transitory computer readable media having instructions stored therein,
   wherein the instructions are executable by the programmable processor to produce a split screen display at the touchscreen display, including—
      an active image area at which images of a patient obtained from ultrasound signals received by the transducer device are displayed, and
      a thumb control area that is accessible by a user's thumb when holding the portable ultrasound system, wherein the control area includes a thumbwheel having one or more controls that can be selectively activated by the user's thumb when holding the portable ultrasound system and are rotatable on and off of the thumb control area.

2. The portable ultrasound system of claim 1 wherein the one or more controls on the thumbwheel include controls for changing at least one of a gain, scan depth, and imaging mode of the ultrasound scan.

3. The portable ultrasound system of claim 1 wherein the one or more controls on the thumbwheel include touch-selectable panels.

4. The portable ultrasound system of claim 1 wherein the processor is configured to execute instructions that display a slider feature adjacent to the thumbwheel; wherein the slider feature can be operated with the user's thumb when holding the portable ultrasound system.

5. The portable ultrasound system of claim 4 wherein the processor is configured to execute instructions that detect movement of the user's thumb generally across the slider feature to increase or decrease gain.

6. The portable ultrasound system of claim 4 wherein the processor is configured to execute instructions that detect movement of the user's thumb generally across the slider feature to advance or rewind through a series of image frames displayed at the active area.

7. A method executed by a processor to produce ultrasound images in a portable ultrasound system, the method comprising:
   receiving, from a transducer device, ultrasound signals corresponding to a target area within a patient obtained from an ultrasound scan;
   displaying an active image on a touchscreen display based on the ultrasound signals;
   displaying a thumb control area on the touchscreen display, wherein the thumb control area includes a thumbwheel having one or more controls that can be selectively activated and are rotatable on and off of the thumb control area;
   detecting movement of a user's thumb on the thumbwheel when the user is holding the portable ultrasound system;
   in response to detecting the movement, rotating individual controls onto and off of the thumb control area; and
   detecting a selection of one of the individual controls.

8. The method of claim 7, further comprising changing at least one parameter of the ultrasound scan based, at least in part, on the selected parameter.

9. The method of claim 8 wherein the parameter includes at least one of a gain, scan depth, and imaging mode.

10. The method of claim 8, further comprising:
overlaying a graphical marker on the active image;
detecting further movement of the user's thumb on the thumb control area; and
moving the graphical marker based on the detected further movement of the user's thumb.

11. The method of claim 7 wherein the user input is a first user input, and wherein the method further comprises:
detecting further movement of the user's thumb on the thumb control area; and
moving a location and/or the size of the thumbwheel based on the detected further movement of the user's thumb.

12. The method of claim 7 wherein displaying the thumb control area further includes displaying a slider feature that can be operated with the user's thumb.

13. The method of claim 12 wherein detecting the movement of the user's thumb includes:
detecting movement of the user's thumb across the slider feature in a first direction to increase gain; and
detecting movement of the user's thumb in a second direction across the slider feature to decrease the gain.

14. The method of claim 12 wherein detecting the movement of the user's thumb includes:
detecting movement of the user's thumb across the slider feature in a first direction to advance through image frames displayed at the active area; and
detecting movement of the user's thumb across the slider feature in a second direction to rewind through the image frames.

* * * * *